(12) United States Patent
Begg

(10) Patent No.: US 10,842,350 B2
(45) Date of Patent: Nov. 24, 2020

(54) ENDOSCOPIC DEVICE WITH DRIP FLANGE AND METHODS OF USE THEREOF FOR AN OPERATIVE PROCEDURE

(71) Applicant: COVIDIEN LP, Mansfield, MA (US)

(72) Inventor: Nikolai D. Begg, Wayland, MA (US)

(73) Assignee: COVIDIEN LP, Mansfield, MA (US)

( * ) Notice: Subject to any disclaimer, the term of this patent is extended or adjusted under 35 U.S.C. 154(b) by 309 days.

(21) Appl. No.: 15/574,421

(22) PCT Filed: Jun. 13, 2016

(86) PCT No.: PCT/US2016/037222
§ 371 (c)(1),
(2) Date: Nov. 15, 2017

(87) PCT Pub. No.: WO2016/205126
PCT Pub. Date: Dec. 22, 2016

(65) Prior Publication Data
US 2018/0132702 A1 May 17, 2018

Related U.S. Application Data

(60) Provisional application No. 62/180,972, filed on Jun. 17, 2015.

(51) Int. Cl.
*A61B 1/00* (2006.01)
*A61B 1/015* (2006.01)
(Continued)

(52) U.S. Cl.
CPC ...... *A61B 1/00071* (2013.01); *A61B 1/00135* (2013.01); *A61B 1/00137* (2013.01);
(Continued)

(58) Field of Classification Search
None
See application file for complete search history.

(56) References Cited

U.S. PATENT DOCUMENTS 1,585,934 A  5/1926  Muir
1,666,332 A  4/1928  Hirsch
(Continued)

FOREIGN PATENT DOCUMENTS

DE  3339322 A1  5/1984
DE  3206381 C2  7/1986
(Continued)

OTHER PUBLICATIONS

European Examination Report issued in corresponding European Application No. 16736303.5 dated May 2, 2019, 5 pages.

*Primary Examiner* — Timothy J Neal
(74) *Attorney, Agent, or Firm* — Carter, DeLuca & Farrell LLP

(57) ABSTRACT

Systems and methods herein are directed to an endoscopic device with a drip flange, including the assembly and use of the endoscopic device. The endoscopic device with a drip flange may be positioned to abut an aperture into an operative cavity and inserted through the aperture. An endoscopic procedure may be performed, during which fluid moves along an outside surface of the elongate shaft, the fluid moving from the distal end toward the proximal end, and where the fluid is directed to a drip flange coupled to the outside surface of the elongate shaft between the distal tip and a proximal end of the elongate shaft.

13 Claims, 8 Drawing Sheets

(51) Int. Cl.
*A61B 1/317* (2006.01)
*A61B 1/303* (2006.01)

(52) U.S. Cl.
CPC .............. *A61B 1/015* (2013.01); *A61B 1/303* (2013.01); *A61B 1/317* (2013.01); *A61B 1/00073* (2013.01)

(56) References Cited

U.S. PATENT DOCUMENTS

| | | | |
|---|---|---|---|
| 1,831,786 A | | 11/1931 | Duncan |
| 2,224,464 A | * | 12/1940 | Wolf ................... A61B 1/2676 606/45 |
| 2,708,437 A | * | 5/1955 | Hutchins ............ A61B 1/00135 600/104 |
| 3,297,022 A | | 1/1967 | Wallace |
| 3,686,706 A | | 8/1972 | Finley |
| 3,734,099 A | | 5/1973 | Bender et al. |
| 3,791,379 A | | 2/1974 | Storz |
| 3,812,855 A | | 5/1974 | Banko |
| 3,835,842 A | | 9/1974 | Iglesias |
| 3,850,162 A | | 11/1974 | Iglesias |
| 3,945,375 A | | 3/1976 | Banko |
| 3,980,252 A | | 9/1976 | Tae |
| 3,995,619 A | | 12/1976 | Glatzer |
| 3,996,921 A | | 12/1976 | Neuwirth |
| 4,011,869 A | | 3/1977 | Seiler, Jr. |
| 4,108,182 A | | 8/1978 | Hartman et al. |
| 4,146,405 A | | 3/1979 | Timmer et al. |
| 4,198,958 A | | 4/1980 | Utsugi |
| 4,203,444 A | | 5/1980 | Bonnell et al. |
| 4,210,146 A | | 7/1980 | Banko |
| 4,246,902 A | | 1/1981 | Martinez |
| 4,247,180 A | | 1/1981 | Norris |
| 4,258,721 A | | 3/1981 | Parent et al. |
| 4,261,346 A | | 4/1981 | Wettermann |
| 4,294,234 A | | 10/1981 | Matsuo |
| 4,316,465 A | | 2/1982 | Dotson, Jr. |
| 4,369,768 A | | 1/1983 | Vukovic |
| 4,392,485 A | | 7/1983 | Hiltebrandt |
| 4,414,962 A | | 11/1983 | Carson |
| 4,449,538 A | | 5/1984 | Corbitt et al. |
| 4,493,698 A | | 1/1985 | Wang et al. |
| 4,517,977 A | | 5/1985 | Frost |
| 4,543,965 A | | 10/1985 | Pack et al. |
| 4,567,880 A | | 2/1986 | Goodman |
| 4,589,414 A | | 5/1986 | Yoshida et al. |
| 4,601,284 A | | 7/1986 | Arakawa et al. |
| 4,601,290 A | | 7/1986 | Effron et al. |
| 4,606,330 A | | 8/1986 | Bonnet |
| 4,624,243 A | * | 11/1986 | Lowery ............... A61B 1/00165 600/114 |
| 4,630,598 A | | 12/1986 | Bonnet |
| 4,644,952 A | | 2/1987 | Patipa et al. |
| 4,649,919 A | | 3/1987 | Thimsen et al. |
| 4,700,694 A | | 10/1987 | Shishido |
| 4,706,656 A | | 11/1987 | Kuboto |
| 4,718,291 A | | 1/1988 | Wood et al. |
| 4,737,142 A | | 4/1988 | Heckele |
| 4,749,376 A | | 6/1988 | Kensey et al. |
| 4,756,304 A | * | 7/1988 | Watanabe ......... A61B 1/00142 600/112 |
| 4,756,309 A | | 7/1988 | Sachse et al. |
| 4,819,635 A | | 4/1989 | Shapiro |
| 4,844,064 A | | 7/1989 | Thimsen et al. |
| 4,850,354 A | | 7/1989 | McGurk-Burleson et al. |
| 4,856,919 A | | 8/1989 | Takeuchi et al. |
| 4,867,157 A | | 9/1989 | McGurk-Burleson et al. |
| 4,924,851 A | | 5/1990 | Ognier et al. |
| 4,940,061 A | | 7/1990 | Terwilliger et al. |
| 4,950,278 A | | 8/1990 | Sachse et al. |
| 4,955,882 A | | 9/1990 | Hakky |
| 4,971,034 A | | 11/1990 | Doi et al. |
| 4,986,827 A | | 1/1991 | Akkas et al. |
| 4,998,527 A | | 3/1991 | Meyer |
| 4,998,914 A | | 3/1991 | Wiest et al. |
| 5,007,917 A | | 4/1991 | Evans |
| 5,027,792 A | | 7/1991 | Meyer |
| 5,037,386 A | | 8/1991 | Marcus et al. |
| 5,105,800 A | | 4/1992 | Takahashi et al. |
| 5,106,364 A | | 4/1992 | Hayafuji et al. |
| 5,112,299 A | | 5/1992 | Pascaloff |
| 5,116,868 A | | 5/1992 | Chen et al. |
| 5,125,910 A | | 6/1992 | Freitas |
| 5,133,713 A | | 7/1992 | Huang et al. |
| 5,152,744 A | | 10/1992 | Krause et al. |
| 5,158,553 A | | 10/1992 | Berry et al. |
| 5,163,433 A | | 11/1992 | Kagawa et al. |
| 5,169,397 A | | 12/1992 | Sakashita et al. |
| 5,176,677 A | | 1/1993 | Wuchinich |
| 5,195,541 A | | 3/1993 | Obenchain |
| 5,226,910 A | | 7/1993 | Kajiyama et al. |
| 5,244,459 A | | 9/1993 | Hill |
| 5,254,117 A | | 10/1993 | Rigby et al. |
| 5,269,785 A | | 12/1993 | Bonutti |
| 5,270,622 A | | 12/1993 | Krause |
| 5,275,609 A | | 1/1994 | Pingleton et al. |
| 5,288,290 A | | 2/1994 | Brody |
| 5,304,118 A | | 4/1994 | Trese et al. |
| 5,312,399 A | | 5/1994 | Hakky et al. |
| 5,312,425 A | | 5/1994 | Evans et al. |
| 5,312,430 A | | 5/1994 | Rosenbluth et al. |
| 5,320,091 A | | 6/1994 | Grossi et al. |
| 5,347,992 A | | 9/1994 | Pearlman et al. |
| 5,350,390 A | | 9/1994 | Sher |
| 5,364,395 A | | 11/1994 | West, Jr. |
| 5,374,253 A | | 12/1994 | Bums, Sr. et al. |
| 5,390,585 A | | 2/1995 | Ryuh |
| 5,392,765 A | | 2/1995 | Muller |
| 5,395,313 A | | 3/1995 | Naves et al. |
| 5,403,276 A | | 4/1995 | Schechter et al. |
| 5,409,013 A | | 4/1995 | Clement |
| 5,409,453 A | | 4/1995 | Lundquist et al. |
| 5,411,513 A | | 5/1995 | Ireland et al. |
| 5,421,819 A | | 6/1995 | Edwards et al. |
| 5,425,376 A | | 6/1995 | Banys et al. |
| 5,429,601 A | | 7/1995 | Conley et al. |
| 5,435,805 A | | 7/1995 | Edwards et al. |
| 5,443,476 A | | 8/1995 | Shapiro |
| 5,449,356 A | | 9/1995 | Walbrink et al. |
| 5,456,673 A | | 10/1995 | Ziegler et al. |
| 5,456,689 A | | 10/1995 | Kresch et al. |
| 5,483,951 A | | 1/1996 | Frassica et al. |
| 5,490,819 A | | 2/1996 | Nicholas et al. |
| 5,490,860 A | | 2/1996 | Middle et al. |
| 5,492,537 A | | 2/1996 | Vancaillie |
| 5,498,258 A | | 3/1996 | Hakky et al. |
| 5,527,331 A | | 6/1996 | Kresch et al. |
| 5,549,541 A | | 8/1996 | Muller |
| 5,556,378 A | | 9/1996 | Storz et al. |
| 5,563,481 A | | 10/1996 | Krause |
| 5,569,164 A | | 10/1996 | Lurz |
| 5,569,254 A | | 10/1996 | Carlson et al. |
| 5,569,284 A | | 10/1996 | Young et al. |
| 5,575,756 A | | 11/1996 | Karasawa et al. |
| 5,586,973 A | | 12/1996 | Lemaire et al. |
| 5,591,187 A | | 1/1997 | Dekel |
| 5,601,583 A | | 2/1997 | Donahue et al. |
| 5,601,603 A | | 2/1997 | Illi |
| 5,602,449 A | | 2/1997 | Krause et al. |
| 5,603,332 A | | 2/1997 | O'Connor |
| 5,630,798 A | | 5/1997 | Beiser |
| 5,649,547 A | | 7/1997 | Ritchart et al. |
| 5,669,927 A | | 9/1997 | Boebel et al. |
| 5,672,945 A | | 9/1997 | Krause |
| 5,674,179 A | | 10/1997 | Bonnet et al. |
| 5,676,497 A | | 10/1997 | Kim |
| 5,695,448 A | | 12/1997 | Kimura et al. |
| 5,702,420 A | | 12/1997 | Sterling et al. |
| 5,709,698 A | | 1/1998 | Adams et al. |
| 5,730,752 A | | 3/1998 | Alden et al. |
| 5,733,298 A | | 3/1998 | Berman |
| 5,741,286 A | | 4/1998 | Recuset |
| 5,741,287 A | | 4/1998 | Alden et al. |

(56) References Cited

U.S. PATENT DOCUMENTS

| | | |
|---|---|---|
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B2 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 2005/0203342 A1* | 9/2005 | Kucklick ............ A61M 1/0084 600/156 |
| 2005/0234298 A1* | 10/2005 | Kucklick ............ A61B 1/00135 600/156 |
| 2006/0293559 A1* | 12/2006 | Grice, III ........... A61B 1/00135 600/102 |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0010299 A1 | 1/2010 | Bakos et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2011/0264129 A1* | 10/2011 | Holdgate ............ A61B 17/3462 606/170 |
| 2012/0067352 A1 | 3/2012 | Gruber et al. |
| 2012/0078038 A1 | 3/2012 | Sahney et al. |
| 2012/0277528 A1* | 11/2012 | Qiao ..................... A61B 1/005 600/109 |
| 2013/0131452 A1 | 5/2013 | Kuroda et al. |
| 2014/0003183 A1 | 1/2014 | Song |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |

(56) References Cited

FOREIGN PATENT DOCUMENTS

| | | |
|---|---|---|
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 200175416 A | 3/2001 |
| JP | 2002529185 A | 9/2002 |
| JP | 2002 538889 A | 11/2002 |
| JP | 2003245247 A | 9/2003 |
| NL | 1006944 C2 | 3/1999 |
| WO | 1981/01648 A1 | 6/1981 |
| WO | 9211816 A2 | 7/1992 |
| WO | 199307821 A1 | 4/1993 |
| WO | 1993/15664 A1 | 8/1993 |
| WO | 1994/26181 A1 | 11/1994 |
| WO | 199505777 A1 | 3/1995 |
| WO | 1995/10981 A1 | 4/1995 |
| WO | 1995/10982 A1 | 4/1995 |
| WO | 1995/22935 A1 | 8/1995 |
| WO | 199530377 A1 | 11/1995 |
| WO | 1996/11638 A1 | 4/1996 |
| WO | 1996/26676 A1 | 9/1996 |
| WO | 199709922 A1 | 3/1997 |
| WO | 1997/17027 A1 | 5/1997 |
| WO | 1997/19642 A1 | 6/1997 |
| WO | 1997/24071 A1 | 7/1997 |
| WO | 199734534 A1 | 9/1997 |
| WO | 199735522 A1 | 10/1997 |
| WO | 9810707 A1 | 3/1998 |
| WO | 199809569 A1 | 3/1998 |
| WO | 199846147 A1 | 10/1998 |
| WO | 199903407 A1 | 1/1999 |
| WO | 199903409 A1 | 1/1999 |
| WO | 199907295 A1 | 2/1999 |
| WO | 1999/11184 A1 | 3/1999 |
| WO | 199939648 A1 | 8/1999 |
| WO | 199944506 A1 | 9/1999 |
| WO | 199960935 A1 | 12/1999 |
| WO | 2000/12010 A1 | 3/2000 |
| WO | 2000/28890 A1 | 5/2000 |
| WO | 200033743 A1 | 6/2000 |
| WO | 200044295 A1 | 8/2000 |
| WO | 200047116 A1 | 8/2000 |
| WO | 200057797 A1 | 10/2000 |
| WO | 2001/35831 A1 | 5/2001 |
| WO | 2001/58368 A1 | 8/2001 |
| WO | 01/95810 A2 | 12/2001 |
| WO | 2002069808 A2 | 9/2002 |
| WO | 2003022164 A1 | 3/2003 |
| WO | 2003077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 200704483 3 A2 | 4/2007 |
| WO | 2012044705 A1 | 4/2012 |

\* cited by examiner

ENDOSCOPIC DEVICE WITH DRIP FLANGE AND METHODS OF USE THEREOF FOR AN OPERATIVE PROCEDURE

CROSS-REFERENCE TO RELATED APPLICATIONS

This application is a U.S. National Stage Application under 35 U.S.C. § 371(a) of PCT/US2016/037222 filed Jun. 13, 2016, which claims the benefit of U.S. Provisional Application No. 62/166,479 titled "Endoscope Insertion Assisted by Fluid Bearing Effect," filed May 26, 2015. Each of these applications is hereby incorporated by reference herein as if reproduced in full below.

BACKGROUND

Medical endoscopes are inserted into a patient either through an orifice, incision, or other entry point. In certain procedures that use an endoscope, for example, hysteroscopy, the endoscope is inserted into a cavity filled with patient or surgical fluids. During the procedure, fluid pressure may cause fluid to leak out of the cavity through openings, including the opening through which the endoscope is used. Leaking fluid may travel down the length of the endoscope and drip onto the physician or the floor, presenting a hazard.

SUMMARY

In an embodiment, a method of performing a surgical procedure, comprising: positioning a distal tip of an endoscopic device to abut an aperture into an operative cavity, the endoscopic device defines a central axis, a proximal end, a distal end, a distal tip, and an elongate shaft extending from the distal tip towards the proximal end; inserting the distal tip of the endoscopic device through the aperture; performing an endoscopic procedure while fluid moves along an outside surface of the elongate shaft, the fluid moving from the distal end toward the proximal end; and directing fluid to a drip flange coupled to the outside surface of the elongate shaft between the distal tip and a proximal end of the elongate shaft.

In an embodiment, a system comprising: a sheath comprising an elongate shaft that defines a central axis, a proximal end, and a distal end; an endoscope comprising a proximal end and a distal end, wherein the endoscope is telescoped at least partially within the sheath; a view port defined on the proximal end of the endoscope; a visualization conduit that extends through an optical channel and into the view port; a fluid port defined on the proximal end of the sheath; and a drip flange defined on the elongate shaft between the proximal end and the distal end of the elongate shaft.

In an alternate embodiment, a system comprising: an endoscopic device that defines a central axis, a proximal end, a distal end, an inflow channel, an outflow channel, and an elongate shaft that defines a proximal end and a distal end; a fluid port defined on the proximal end and in fluid communication with the outflow channel; an inflow port defined on the proximal end in communication with the inflow channel; and a drip flange defined on the elongate shaft between the proximal end and the distal end of the elongate shaft.

BRIEF DESCRIPTION OF THE DRAWINGS

For a detailed description of exemplary embodiments, reference will now be made to the accompanying drawings in which.

DEFINITIONS

Figure 1:
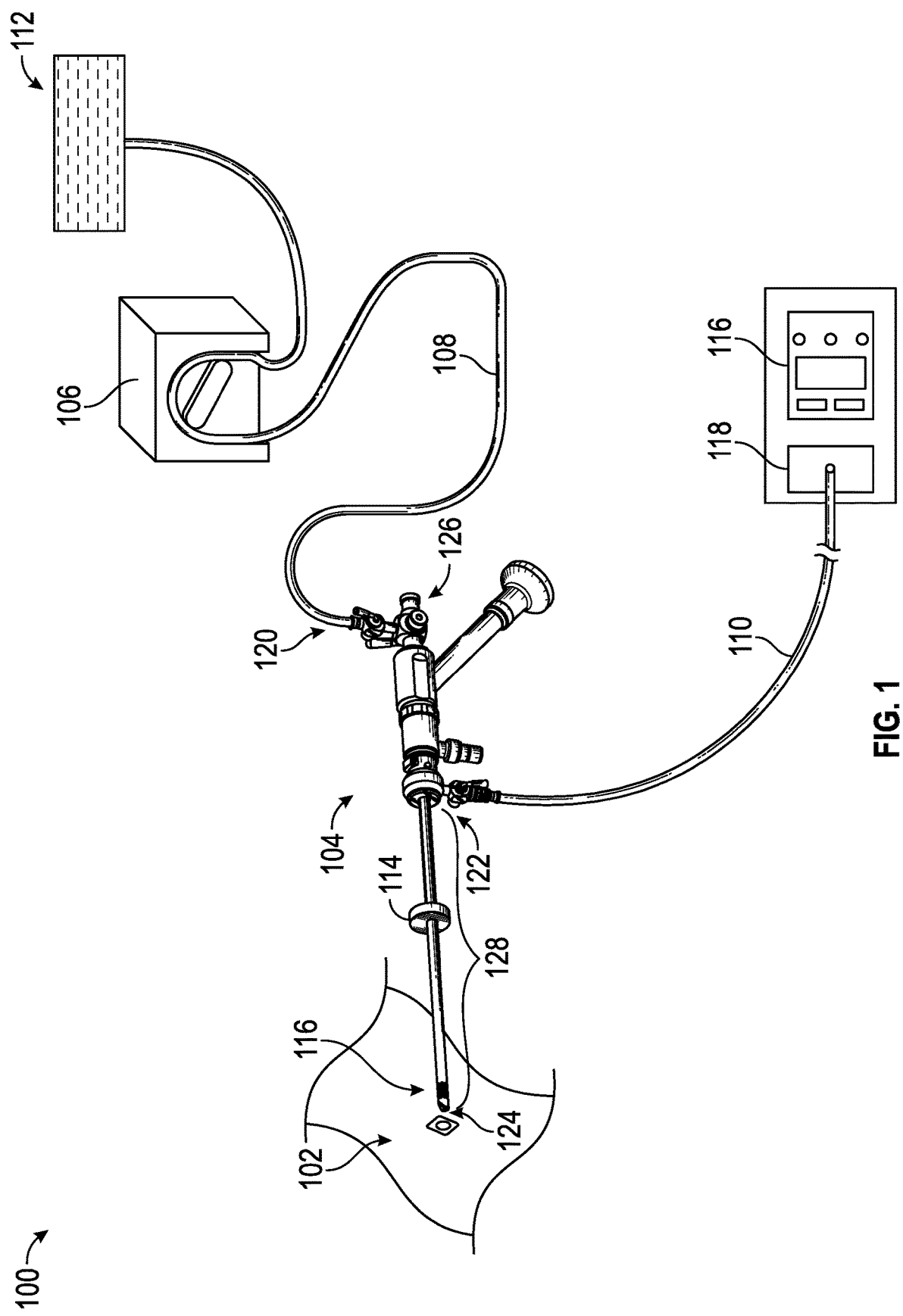
FIG. 1 shows an endoscopic system according to certain embodiments of the present disclosure.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

"Endoscopic device" shall mean an endoscope alone, a sheath alone, or a combination device comprising an endoscope telescoped within a sheath.

"Above," in relation to a fluid bag (e.g., saline bag) and a component, shall mean the fluid bag has a higher elevation than the recited component measured with respect to local gravity.

"Drip flange" shall mean a component disposed on an outside surface of an elongate shaft of an endoscopic device where the drip flange defines an outer dimension greater than an outside diameter of the elongate shaft. For at least some orientations of the endoscopic device, the drip flange is configured to force fluid that encounters the drip flange to drip from or stream from the drip flange rather than run past the drip flange and back onto the outside surface of the elongate shaft downstream of the drip flange.

"Removably coupled" shall mean a first component coupled to a second component such that first component can be decoupled from the second component without destroying or rendering the first or second components non-functional.

"Monolithic," with respect to a drip flange, shall mean a drip flange that is formed as an integral part of an endoscopic device.

"Drip edge" shall mean a portion of a drip flange that acts as a drip point for fluid.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Medical endoscopes are often inserted into cavities filled with patient or surgical fluids. In an operative hysteroscopy, an endoscopic device is inserted into the patient's uterus to view and treat various pathologies. A space in which to navigate is created by injecting fluid at a pressure that causes the uterus to expand. This fluid is often circulated to clear debris during the procedure. Although this endoscopic procedure permits the surgeon to perform the procedure, the procedure creates risk for the patient since fluid may be absorbed into the bloodstream at high pressures and cause life-threatening physiological states. As a result, physicians routinely monitor the difference in the fluid flowing in and out of the patient throughout the procedure. Drapes are used to collect fluid which may be accidentally lost during the procedure to ensure an accurate fluid volume measurement.

As an example, when an endoscopic device is inserted through a patient's cervix, the cervix expands circumferentially to accommodate the scope, effectively creating a seal. Depending on the pressure used, the diameter of the scope, and other factors, the fluid may leak between the scope and the cervix. In hysteroscopy, the scope is often positioned with its distal tip elevated, and the surgeon seated and holding the scope. As a result, leaked fluid often drips down the length of the scope and onto the surgeon, floor, or camera. This fluid leakage may lead to an inability to accurately monitor fluid in and out of the patient, and may interfere with the surgeon's vision if the camera becomes flooded. Further, in cases where leakage is difficult to prevent, drapes, absorbent pads, protective covers, and personal protective equipment are used to keep fluid from the floor, equipment, or operating room staff.

At least in accordance with some embodiments, a drip flange comprising a drip edge is added to an endoscope to arrest or redirect the flow of fluid adhering to the outer surface of the endoscope. The drip flange prevents fluid from reaching tubing, electronics, attached equipment, or other locations where the fluid might negatively impact the patient, user, or procedure. The drip flange may be permanently, removably, or adjustably coupled to the endoscopic device. In some embodiments, the drip flange may be formed as an integral part of an endoscopic device.

In an embodiment, the drip flange defines a conical frustum shape that defines a central axis, a proximal end, and a distal end, wherein an outer diameter of the proximal end is larger than an outer diameter of the endoscopic device. In an alternate embodiment, the drip flange defines a disc shape that defines a central axis, a proximal side, and a distal side, wherein an outer diameter of the proximal end of the drip flange mechanism is larger than an outer diameter of the endoscopic device. The disc-shaped drip flange may comprise a flat distal surface on the distal side relative to a plane perpendicular to the central axis. In alternate embodiments, disc-shaped drip flange may comprise a concave or convex distal surface on the distal side relative to a plane perpendicular to the central axis.

FIG. 1 shows an example endoscopic system 100. In an embodiment, the system 100 comprises an endoscopic device 104 comprising an elongate shaft 128, and a distal tip 116 which is inserted through an aperture 102. In the example, the endoscopic device 104 is connected to a fluid pump 106 and a fluid reservoir 112 (such as a saline bag) by way of a first fluid line 108 that is coupled to a first fluid port 120. In various embodiments, the fluid pump 106 may be fluidly coupled to a separate fluid reservoir 112, and in alternate embodiments the fluid pump 106 may comprise a fluid reservoir. The fluid pump 106 may in some embodiments be a peristaltic pump (as shown), a positive displacement pump, or a centrifugal pump, any of which may be employed to generate fluid inflow. In other embodiments, the fluid pump 106 may be omitted and the fluid reservoir 112 may be in direct fluid communication with the first fluid port 120 and/or a second fluid port 122.

The second fluid port 122 may be in communication with a fluid path such as a fluid outflow path. In the example embodiment, the second fluid line 110 may be coupled to a suction mechanism such as a suction wall pump 118, which may be a stand-alone feature or which may be part of a unit that may include a plurality of other controls for power, display, and adjustment of rate of fluid flow. During an operative procedure, fluid may leak from the aperture 102 along an outside surface of the elongate shaft 128 towards the proximal end 126 of the endoscopic device 104. In an effort to direct this fluid flow away from the proximal end 126, a drip flange may be employed to direct the fluid flow away from the proximal end 126 of the endoscopic device 104. In this example, the fluid flow is directed away from the proximal end 126 such that it does not touch the proximal end 126 of the endoscopic device 104.

In a hysteroscopy procedure, the distal end 124 of endoscopic device 104 is inserted into an aperture 102 that may be a patient's cervix. The patient's cervix 102 may expand circumferentially to accommodate the endoscopic device 104, and effectively create a seal. The drip flange 114 is located on the elongate shaft 128 of the endoscopic device 104, and outside the body of the patient and is not in contact with the patient during the procedure. The drip flange 114 receives and redirects fluid away from the proximal end 126 when the fluid leaks out of the cervix 102 and down the outside surface of the elongate shaft 128.

In alternate embodiments, the drip flange 114 may be permanently coupled to the elongate shaft 128 of the endoscopic device 104 or may be a disposable component. The drip flange 114 may be coupled to the endoscopic device 104 between the proximal end 126 and the distal end 124 but is not in direct contact with the distal end 126. In various embodiments, the drip flange 114 may be (1) formed as an integral part of the endoscopic device 104, (2) removably coupled to the endoscopic device 104, (3) permanently coupled to the endoscopic device 104, and/or (4) adjustable along the elongate sheath 128, or combinations thereof. In one example, the drip flange 114 may be permanently coupled to the endoscopic device 104 in that it cannot be removed without being destroyed or destroying the endoscopic device 104 but where the drip flange 114 is adjustable along a portion of the elongate sheath 128. In another example, the drip flange 114 may be removably coupled to the endoscopic device 104 in and is removed without being destroyed and without destroying the endoscopic device 104.

Figure 2:
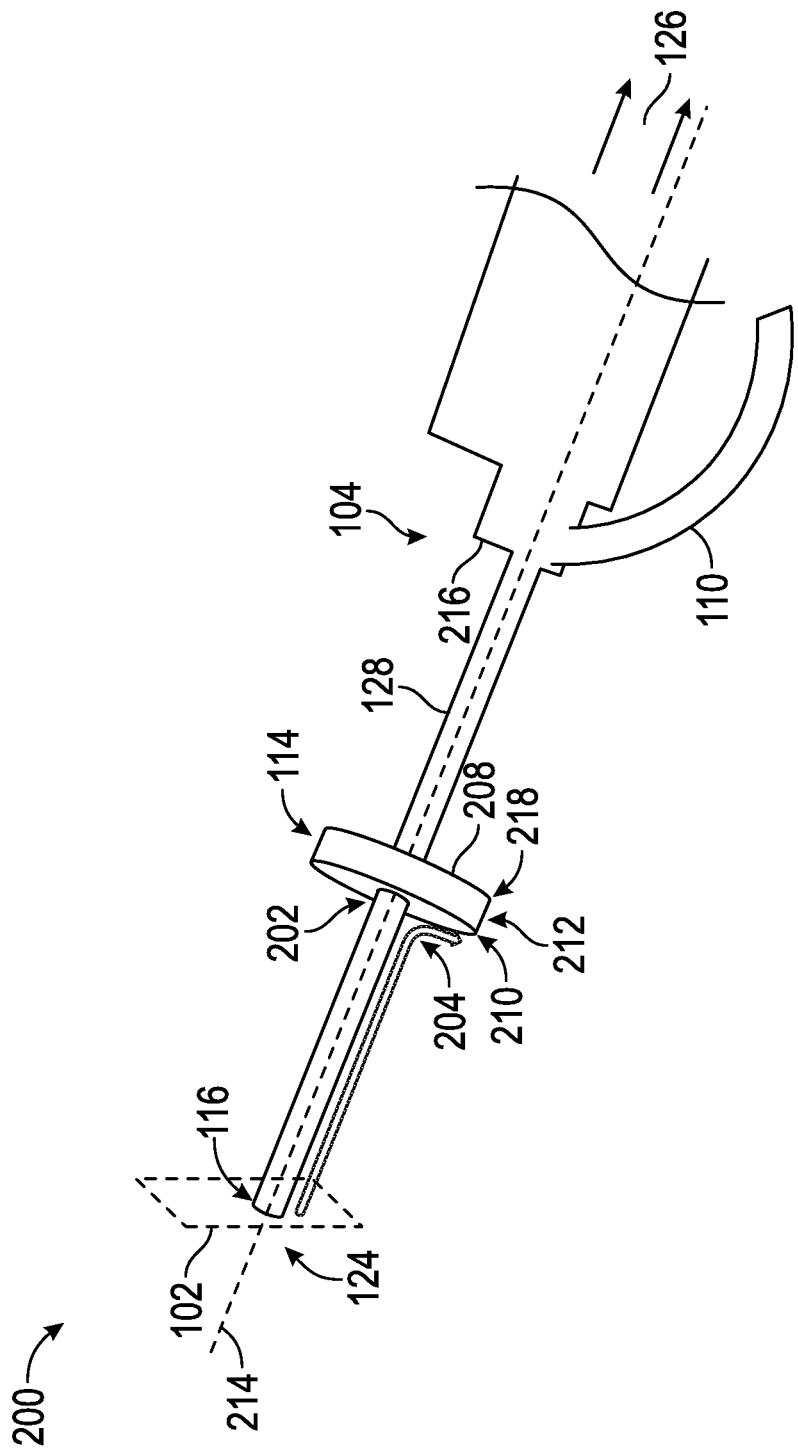
FIG. 2 is an elevation, partial perspective view of the endoscopic system according to certain embodiments of the present disclosure.

FIG. 2 is an elevated partial perspective view 200 of a tissue removal system and illustrates a partial view of the endoscopic device 104, and that the distal end 116 is inserted through the aperture 102. In an embodiment, the endoscopic device comprises a central axis 214, the distal end 124, the distal tip 116, and the elongate shaft 128. The elongate shaft 128 comprises the central axis 214, the distal tip 116, and a proximal end 216 of the elongate draft 128. The drip flange 114 may be disposed along the elongate shaft 128 at a predetermined distance from the distal tip 116 and is not in contact with nor coupled to the proximal end 216 of the elongate shaft 128. The drip flange 114 is positioned such that, when the endoscopic device is in use, the drip flange 114 does not form a seal with or restrict fluid from exiting the aperture 102.

The drip flange 114 comprises the central axis 214 shared with the endoscopic device 104, an interior surface that may comprise a coupling mechanism (not shown), a distal side 202, a proximal side 208, and a transition surface 212 comprising a smooth transition area extending radially from the proximal side 208 to the distal side 202. In some embodiments, where a distal end diameter is less than a proximal end diameter, the component may be defined by a shape of a sphere, conical frustum, disc, pyramid, polygon, or combinations thereof.

The drip flange 114 may be formed as a monolithic piece with a sheath (not separately shown) of the endoscopic device 104. In an alternate embodiment, the drip flange 114 may be adjustably and/or removably coupled to an elongate shaft 128 of a sheath of the endoscopic device 104. The drip flange 114 may be fabricated as a single piece or as a multiple-component piece comprising drains and/or sponges as discussed in detail herein.

In an example disc drip flange 114 illustrated in FIG. 2, the surfaces corresponding to each of the proximal 208 and distal 202 sides of the drip flange 114 may be flat, converse, or concave, or combinations thereof, where a flat surface is defined as perpendicular with respect to the central axis 214. FIG. 2 further illustrates that the distal tip 124 is located above the proximal end 126, indicated by the arrows since FIG. 2 is a partial view. There is a fluid flow 204 established along an outside surface of the elongate shaft 128 from the distal end 124 towards the distal side 202 of the drip flange 114. The fluid flow 204 exits the endoscopic device 104 at a drip edge 210 of the drip flange, and does not contact the proximal end 216 of the elongate shaft 128, nor the proximal end 126 of the endoscopic device 104.

In an embodiment, when fluid leaks from the aperture 102, it travels along at least a portion of the fluid path 204 along the elongate shaft 128 towards the drip flange 114. In an embodiment, if the distal side 202 comprises a concave surface relative to a plane perpendicular to the central axis 214, the fluid collects in the drip flange 114 on the distal side and may drip along drip edge 210 and/or the transition surface 212. In an embodiment, the fluid drips from a point on the drip flange 114 and can then be captured to monitor fluid volume or disposed of in a receptacle (not shown). In an alternate embodiment, a second drip edge 218 may exist at the boundary of the proximal side 208 of the drip flange 114. The second drip edge 218 may be employed in various embodiments, for example, when the transitional surface 212 is at an angle other than parallel to the central axis 214.

Figure 3A:
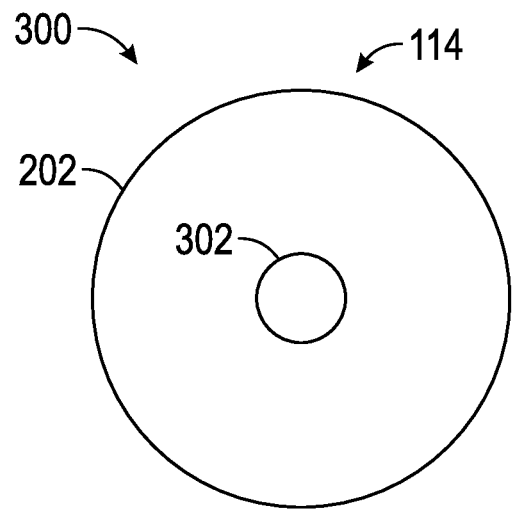
FIGS. 3A and 3B are magnified views of a drip flange according to certain embodiments of the present disclosure.
Figure 3B:
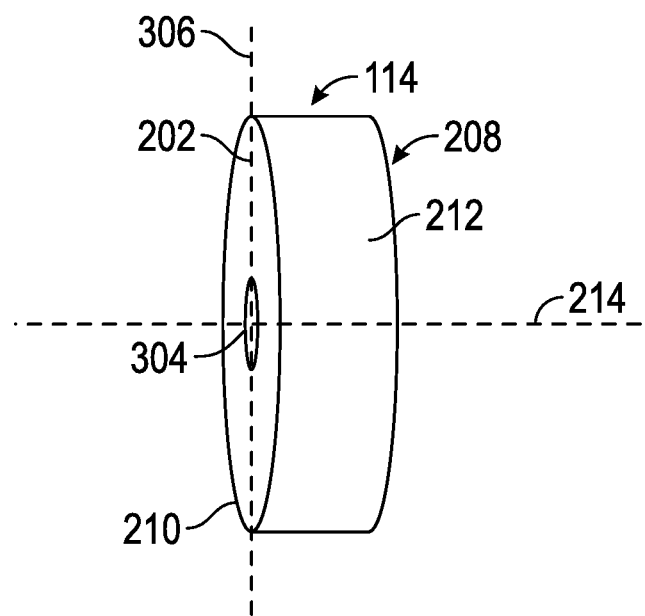

FIGS. 3A and 3B are magnified views of a drip flange 114. FIGS. 3A and 3B illustrate the drip flange 114 in the shape of a disc. The drip flange 114 may comprise the drip edge 210, the distal side 202, the transition surface 212, the proximal side 208, the central axis 214, a through-hole or bore 302 defined by an interior surface 304. In an embodiment, there may be mating features disposed on the interior surface 304 of the bore 302 may permanently or removably couple to the elongate shaft of an endoscopic device. In some embodiments, the position of the drip flange may be adjustable along a length of the elongate shaft. In alternate embodiments, the drip flange may be formed as an integral part of the endoscopic device.

In an embodiment, at least one of the proximal side 208 and the distal side 202 may be defined by surfaces that are perpendicular with respect to the central axis. In alternate embodiments (not shown), the distal side 202 and/or the proximal surface may be concave or convex with respect to a reference line 306 perpendicular to the central axis 214. In various embodiments, the drip flange 114 may be coupled to an endoscopic device 104 when the drip flange 114 is telescoped over the endoscopic device, which may be an endoscope, a sheath, and/or an endoscope telescoped through a sheath.

Figure 4:
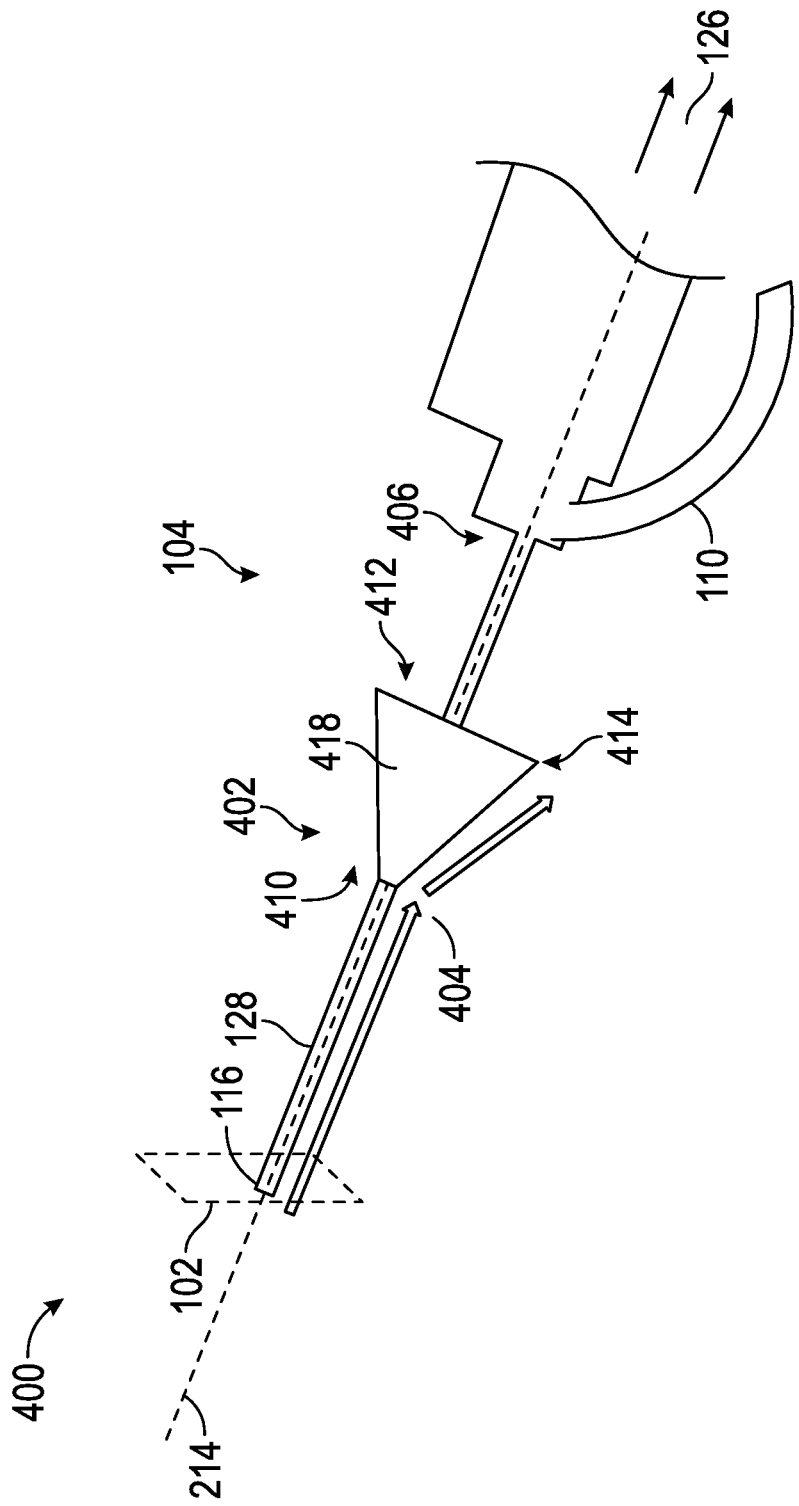
FIG. 4 is an elevation, partial perspective view of an endoscopic system according to certain embodiments of the present disclosure.

FIG. 4 is a partial perspective view 400 of an endoscopic system. In particular, FIG. 4 shows a partial view of the endoscopic device 104, and that the distal end 116 is inserted through the aperture 102. In an embodiment, the endoscopic device comprises a central axis 214, the distal end 124, the distal tip 116, and the elongate shaft 128. The elongate shaft 128 comprises the central axis 214, the distal tip 116, and a proximal end 216 of the elongate draft 128, and a drip flange 402 is coupled to the elongate shaft 128.

The drip flange 402 may be formed as a monolithic piece with the endoscopic device 104, or may be a component 402 that is adjustably and/or removably coupled to a length of an elongate shaft 128 of the endoscopic device 104. A drip flange 402 in the shape of a conical frustum is illustrated in FIG. 4. The drip flange 402 comprises the central axis 214 shared with the endoscopic device 104, an interior surface that may comprise a coupling mechanism (not shown), a distal end 410, a proximal end 412, and an outside surface 418 comprising a smooth transition area extending radially from the proximal end 412 to the distal end 410 and that may be referred to as the outside surface 418. In an embodiment, a diameter of the distal end 410 of the drip flange 402 is smaller than a diameter of the proximal end 412.

FIG. 4 further illustrates that the distal tip 124 is located above the proximal end 126, indicated by the arrows since FIG. 4 is a partial view. There is a fluid flow 404 established along an outside surface of the elongate shaft 128 from the distal end 124 towards the distal end 410 of the drip flange 402 along the outside surface 418. The fluid flow 404 exits the endoscopic device 104 at the drip edge 414 of the drip flange 402, and does not contact the proximal end 406 of the elongate shaft 128, nor the proximal end 126 of the endoscopic device 104. The drip flange 402 may be coupled to the elongate shaft 128 between the distal end 116 of the endoscopic device 104 and the proximal end 406 of the elongate shaft 128, and is not in contact with the proximal end 406. In an embodiment, a diameter of the distal end 410 of the drip flange 402 is smaller than a diameter of the proximal end 412.

In FIG. 4, the drip flange 402 is shaped similar a cone, with the distal end 410 positioned at, for example, a 45 degree angle to the elongate shaft 128 and the central axis 214. The drip flange 402 may be coupled to endoscopic device 104 either permanently or removably, and may be reusable or disposable. As fluid leaks out of the aperture 102 and travels along the elongate shaft 128 of the endoscopic device 104, the fluid is redirected to travel down the outside surface 418 of the drip flange 402 and to the drip edge 414.

It is appreciated that the drip edge 414 extends circumferentially around the drip flange 402. The fluid can then be captured to monitor fluid volume or disposed of in a receptacle (not shown). The drip flange 402 prevents leaking fluid from reaching the endoscope tubing 110 or attached equipment (not shown) towards the proximal end 126 of the endoscopic device 104. In an alternative embodiment, a sponge or absorbent feature may be added to the drip flange 402 at the distal end 410, along the outside surface 418, and/or at the drip edge 414 to capture the leaking fluid.

Figure 5:
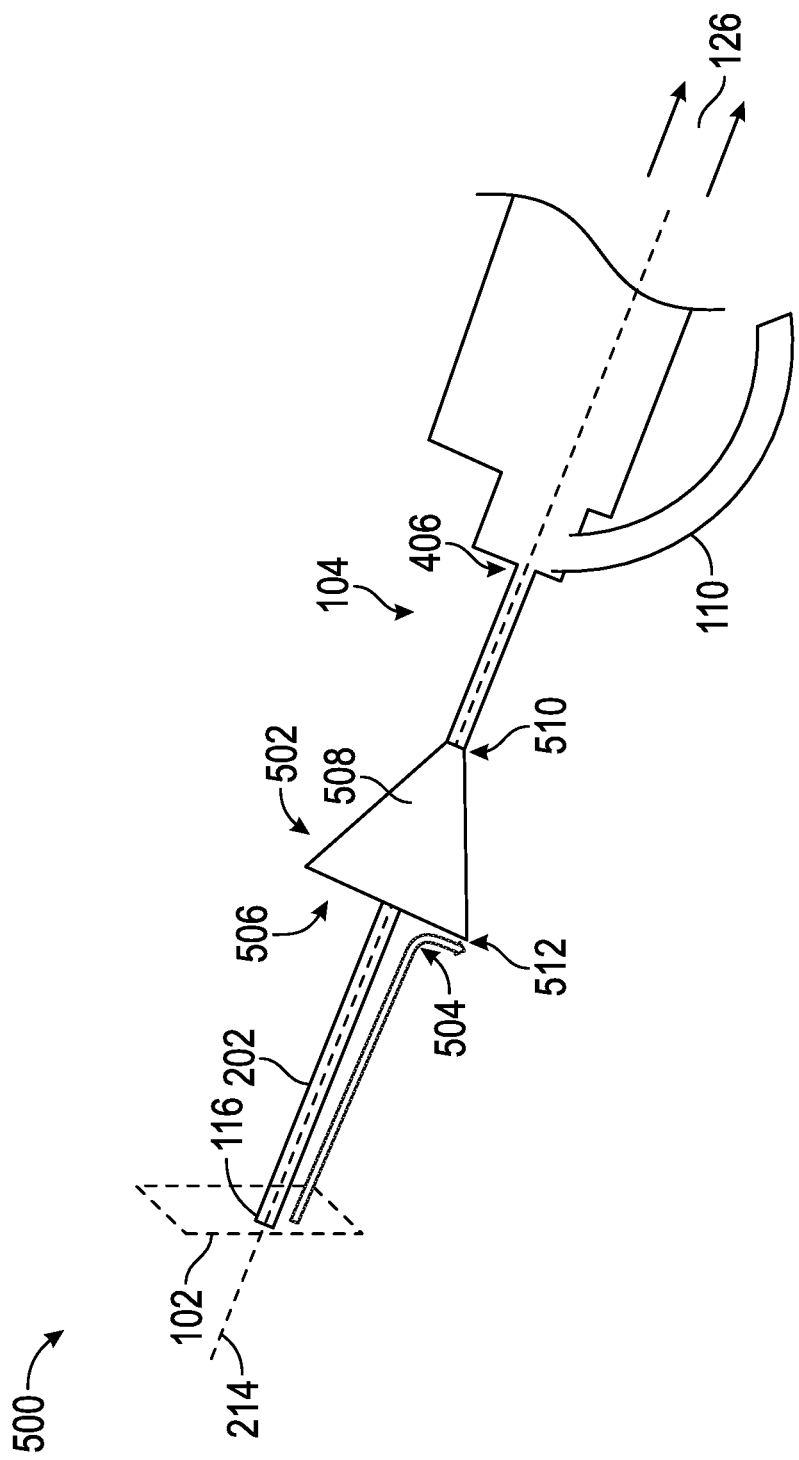
FIG. 5 is an elevation, partial perspective view of an endoscopic system according to certain embodiments of the present disclosure.

FIG. 5 is a partial perspective view 500 of an endoscopic system and illustrates a partial view of the endoscopic device 104, and that the distal end 116 is inserted through the aperture 102. In an embodiment, the endoscopic device 104 comprises a central axis 214, the distal end 124, the distal tip 116, and the elongate shaft 128. The elongate shaft 128 comprises the central axis 214, the distal tip 116, and a proximal end 216 of the elongate draft 128, and a drip flange 502 is coupled to the elongate shaft 128.

The drip flange 502 may be formed as a monolithic piece with the endoscopic device 104, or may be a component 502 that is adjustably and/or removably coupled to the elongate shaft 128 of a sheath of the endoscopic device 104. A drip flange 502 in the shape of a conical frustum is illustrated in FIG. 5. The drip flange 502 comprises the central axis 214 shared with the endoscopic device 104, an interior surface that may comprise a coupling mechanism (not shown), a distal end 506, a proximal end 510, and an outside surface 508 extending radially from the proximal end 510 to the distal end 506. In an embodiment, a diameter of the distal end 506 of the drip flange 502 is larger than a diameter of the proximal end 510.

FIG. 5 further illustrates that the distal tip 124 is located above the proximal end 126, the direction of which is indicated by the arrows since FIG. 5 is a partial view. There is a fluid flow 504 established along an outside surface of the elongate shaft 128 from the distal end 124 along the distal end 506 of the drip flange 502. The fluid flow 504 exits the endoscopic device 104 at the drip edge 512 of the drip flange 502, and the fluid does not contact the proximal end 510 of the elongate shaft 128. In an embodiment, the drip flange 502 does not contact the proximal end 126 of the endoscopic device 104. It is appreciated that the drip edge 512 extends circumferentially around the drip flange 502.

As illustrated by the fluid path 504, as fluid leaks out of the aperture 102 and travels along the outside surface of the elongate shaft 128, the fluid is redirected to travel down the distal end 506 of the drip flange 502 and to the drip edge 512. In some embodiments, the fluid can then be captured to monitor fluid volume or disposed of in a receptacle (not shown). The drip flange 502 prevents fluid from reaching the endoscope tubing 110 or attached equipment (not shown) towards the proximal end 126 of the endoscopic device 104. In an alternative embodiment, a sponge or other absorbent feature may be added to the drip flange 502 at the distal end 506 and/or at the drip edge 512 to capture the leaking fluid.

Figure 6A:
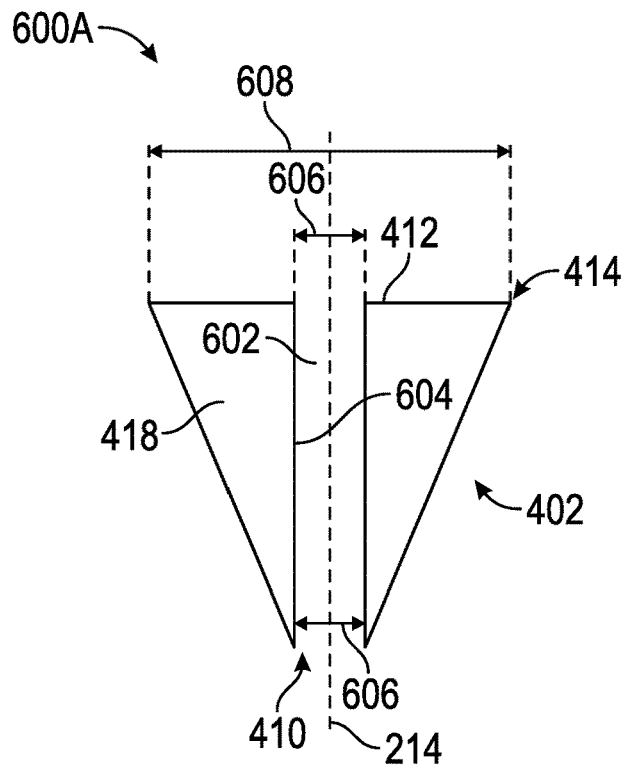
FIG. 6A is a cross-sectional view along the central axis of a drip flange according to certain embodiments of the present disclosure.

FIG. 6A is a cross-sectional view 600A of a conical frustum version of a drip flange. The drip flange 402 in FIG. 6A may be similar to that in FIG. 4. FIG. 6A illustrates the drip flange 402, the central axis 214, a channel 602 extending from the proximal end 412 to the distal end 410, and an interior surface 604 of the channel 602. An interior diameter 606 of the channel 602 may be the same as the diameter of the distal end 410, and an outer diameter 608 of the proximal end 412 is larger than the diameter of the distal end 410. In some embodiments, the interior surface of the channel 602 may comprise mating/coupling features (not pictured) configured to mate with an endoscopic device. In various embodiments, the drip flange 402 may be coupled to an endoscopic device when the drip flange 402 is telescoped over the endoscopic device, which may be in the form of an endoscope, a sheath, and/or an endoscope telescoped through a sheath.

Figure 6B:
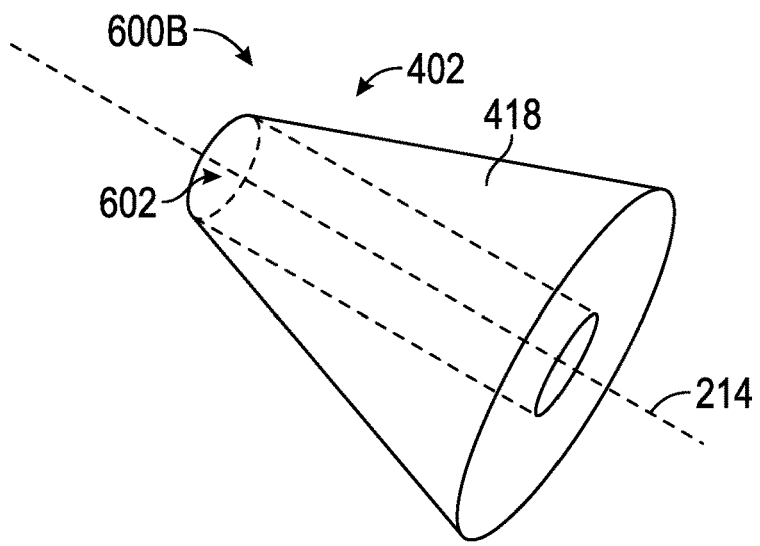
FIG. 6B is a perspective view of a drip flange according to certain embodiments of the present disclosure.

FIG. 6B is a magnified perspective view 600B of a drip flange in the shape of a conical frustum. The drip flange 402 in FIG. 6B may be similar to that in FIG. 4. FIG. 6B illustrates the drip flange 402, and illustrates the channel 602 that extends through the solid body of the drip flange 402. In various embodiments, the drip flange 402 may be coupled to an endoscopic device when the drip flange 402 is telescoped over the endoscopic device, which may be in the form of an endoscope, a sheath, and/or an endoscope telescoped through a sheath. It is appreciated that the discussion above with respect to the solid body and the coupling of the drip flange 402 may also be applied to the drip flange 502 discussed above.

Figure 7:
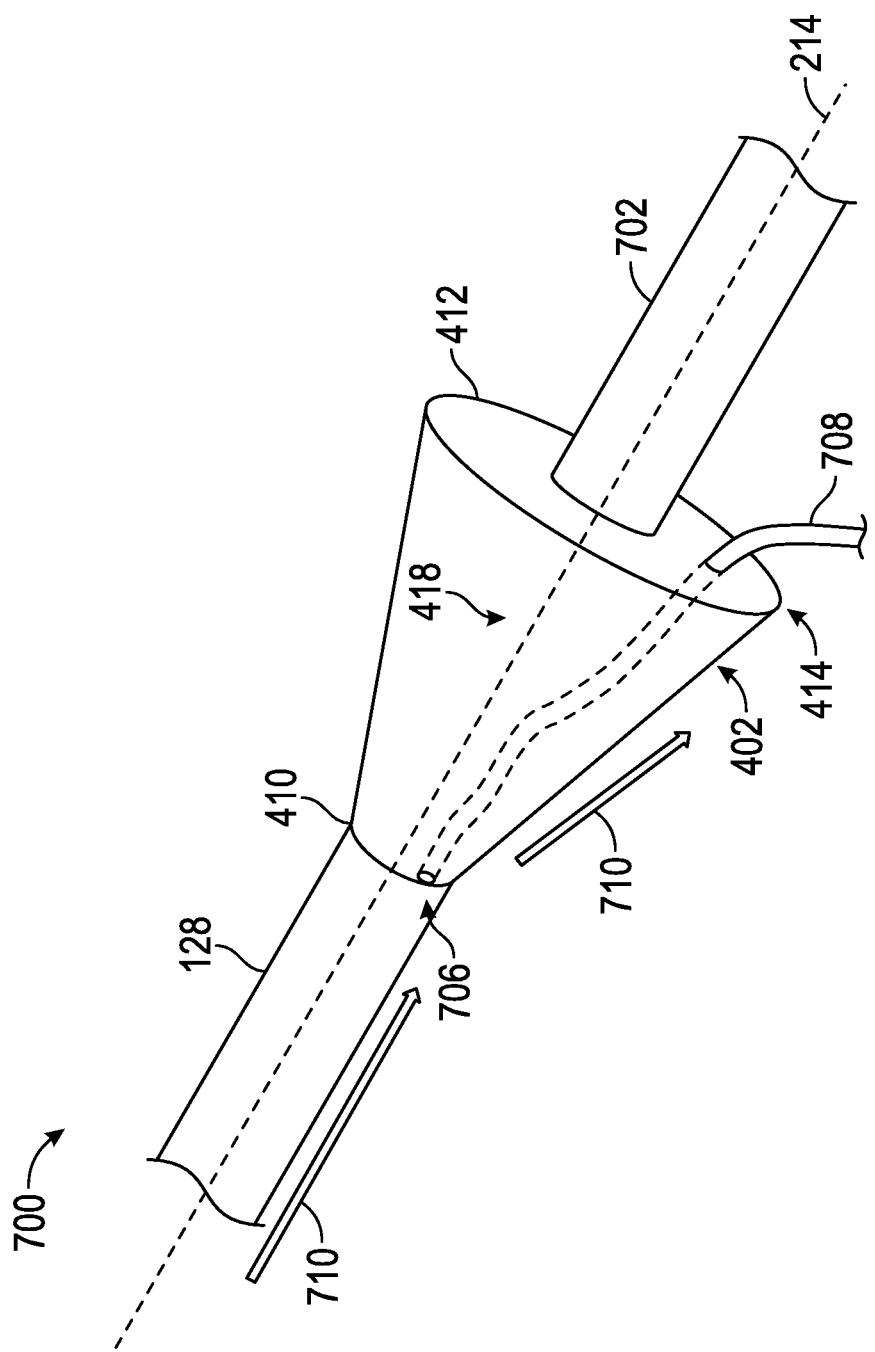
FIG. 7 is an elevation, partial perspective view of an endoscopic system according to certain embodiments of the present disclosure.

FIG. 7 is a partial perspective view of an endoscopic system 700. FIG. 7 illustrates a system 700 coupled to a tubing 708 that comprises a distal end 702 that captures, through pressure or otherwise, the fluid leaking (illustrated by fluid flow 710) from the patient and traveling down elongate shaft 128. The tubing 708 comprises a flexible, rigid, or semi-rigid structure that extends through the drip flange 402 from the distal side 410 through to the proximal end 412. The tubing 708 can be attached to either the elongate shaft 128 and/or the drip flange 402 and/or the drip edge. Once the fluid enters the tubing 708 at the distal side 410 at 706, the fluid can be directed to a receptacle (not shown) in order to monitor fluid flow or it can be disposed of as waste. In an alternative embodiment, a sponge or absorbent feature may be added to the drip flange 402 to capture any leaking fluid that does not travel into the tubing 708.

Figure 8:
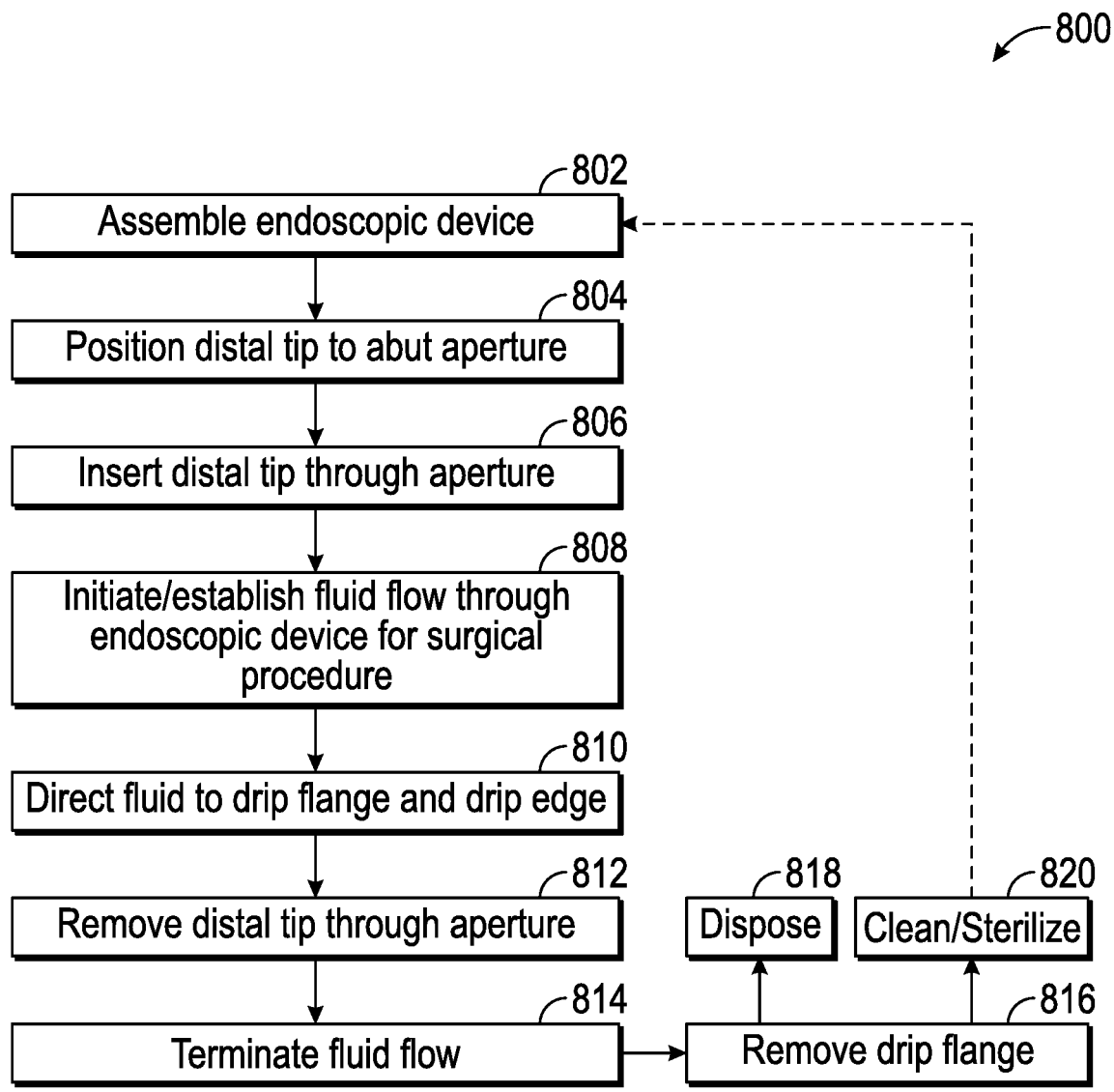
FIG. 8 illustrates a method of performing a surgical procedure according to certain embodiments of the present disclosure.

FIG. 8 illustrates a method 800 of performing a surgical procedure. At block 802, an endoscopic device is assembled. The endoscopic device may be assembled by (1) telescoping an endoscope into a sheath to form the endoscopic device and then telescoping a drip flange over the endoscopic device; (2) telescoping an endoscope into a sheath with a drip flange formed monolithically with the sheath; (3) telescoping the endoscope through the sheath, when the drip flange is one of permanently or removably coupled to the sheath prior to telescoping the endoscope; (4) telescoping the drip flange over the sheath; or (5) telescoping the drip flange over an endoscope.

At block 804, a distal tip of an endoscopic device is positioned to abut an aperture into an operative cavity, the endoscopic device comprises a central axis, a proximal end, a distal end, a distal tip, and an elongate shaft extending from the distal tip towards the proximal end. At block 806, the distal tip of the endoscopic device is inserted through the aperture and fluid flow is initiated and/or established through the endoscopic device at block 808 for a surgical procedure. At block 810, fluid flowing from the aperture is directed from the distal end of the endoscopic device along the elongate shaft and towards the drip flange and the drip edge of the drip flange. At block 812, the distal tip is removed through the aperture and fluid flow is terminated at block 814.

In some embodiments, the drip flange may be removed from the endoscopic device (uncoupled) at block 816 without compromising the functionality of the endoscopic device, and, may be either disposed of at block 818 or cleaned/sterilized/reused at block 820, at which point the method 800 may return to block 802 where the endoscopic device is re-assembled.

The above discussion is meant to be illustrative of the principles and various embodiments of the present invention. Numerous variations and modifications will become apparent to those skilled in the art once the above disclosure is fully appreciated. For example, various combinations of perforations types, number, geometry, and size may be employed in different embodiments and may be employed along varying lengths of the endoscopic device. It is intended that the following claims be interpreted to embrace all such variations and modifications.

What is claimed is:

1. A system comprising:
   a sheath comprising an elongate shaft that defines a central axis, a proximal end, and a distal end;
   an endoscope comprising a proximal end and a distal end, wherein the endoscope is telescoped at least partially within the sheath;
   a view port defined on the proximal end of the endoscope;
   a visualization conduit that extends through an optical channel and into the view port;
   a fluid port defined on the proximal end of the sheath;
   a drip flange defined on the elongate shaft between the proximal end and the distal end of the elongate shaft, the drip flange configured to redirect fluid away from the proximal end of the elongate shaft; and
   tubing coupled to the drip flange, the tubing configured to receive the redirected fluid.

2. The system of claim 1, wherein the drip flange is disposed between the distal end and the proximal end of the elongate shaft.

3. The system of claim 1, wherein the endoscope is telescoped at least partially within the sheath along the central axis to form an endoscopic device, the endoscopic device defines a working inflow channel, a working outflow channel, and an optical channel along a length of the endoscopic device.

4. The system of claim 1, wherein the drip flange is removably coupled to the elongate shaft.

5. The system of claim 1, wherein the drip flange is disposed a predetermined non-zero distance from the proximal end of the elongate shaft.

6. The system of claim 1, wherein the drip flange defines a conical frustum, wherein the conical frustum comprises a first diameter at a distal end and a second diameter at a proximal end, wherein the first diameter is smaller than the second diameter.

7. The system of claim 1, wherein the drip flange defines a conical frustum, wherein the conical frustum comprises a first diameter at a distal end and a second diameter at a proximal end, wherein the first diameter is larger than the second diameter.

8. A system comprising:
   an endoscopic device that defines a central axis, a proximal end, a distal end, an inflow channel, an outflow channel, and an elongate shaft that defines a proximal end and a distal end;
   a fluid port defined on the proximal end and in fluid communication with the outflow channel;
   an inflow port defined on the proximal end in communication with the inflow channel;
   a drip flange defined on the elongate shaft between the proximal end and the distal end of the elongate shaft, the drip flange configured to redirect fluid away from the proximal end of the elongate shaft; and
   tubing coupled to the drip flange, the tubing configured to receive the redirected fluid.

9. The system of claim 8, wherein the endoscopic device comprises an endoscope telescoped in a sheath.

10. The system of claim 9, wherein the drip flange is a monolithic piece with the sheath.

11. The system of claim 9, wherein the drip flange mechanism is removably coupled to an outside surface of the sheath.

12. The system of claim 8, wherein the flange mechanism defines a conical frustum shape, wherein the conical frustum comprises a first diameter at a distal end and a second diameter at a proximal end, wherein the first diameter is smaller than the second diameter.

13. The system of claim 8, further comprising:
   a view port defined on the proximal end of the endoscopic device; and
   a visualization conduit that extends through the optical channel and into the view port.

* * * * *